United States Patent [19]
Renaut et al.

[11] Patent Number: 5,476,870
[45] Date of Patent: Dec. 19, 1995

[54] 15-DEOXYSPERGUALIN ANALOGS, THEIR METHOD OF PREPARATION AND THEIR USE IN THERAPEUTICS

[75] Inventors: Patrice Renaut, Hauteville-lès-Dijon; Luc Lebreton, Dijon; Patrick Dutartre, Longchamp; Philippe Derrepas, Agey; Soth Samreth, Longvic, all of France

[73] Assignee: Fournier Industrie ET Sante, Paris, France

[21] Appl. No.: 161,773

[22] Filed: Dec. 2, 1993

[30] Foreign Application Priority Data

Dec. 2, 1992 [FR] France .................. 92 14517

[51] Int. Cl.$^6$ .................. A61K 31/27
[52] U.S. Cl. .................. 514/482; 514/588; 514/616; 560/159; 564/59; 564/160
[58] Field of Search .................. 560/159; 564/59, 564/160; 514/478, 588, 616, 482

[56] References Cited

U.S. PATENT DOCUMENTS 4,956,504  9/1990  Takeuchi .................. 564/153

FOREIGN PATENT DOCUMENTS 0105193  4/1984  European Pat. Off. .
0347820  12/1989  European Pat. Off. .

OTHER PUBLICATIONS

*Journal of Antibiotics*, vol. 41, No. 11, Nov. 1988, Tokyo, Japan, pp. 1629–1643 R. Nishizawa "Synthesis and Biological Activity of Spergualin Analogues I" *p. 1629, lines 9–15; tables 1–2*.

*Primary Examiner*—Michael L. Shippen
*Attorney, Agent, or Firm*—Ostrolenk, Faber, Gerb & Soffen

[57] ABSTRACT

The present invention relates, by way of novel industrial products, to compounds which are structurally related to 15-deoxyspergualin. These novel compounds have the formula

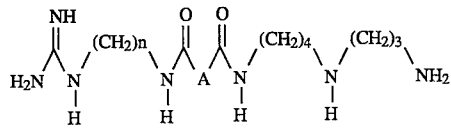

in which:

n is equal to 6 or 8 and

A is a single bond, $CH_2$, CHF, CH(OH), CH(OCH$_3$), CH$_2$NH or CH$_2$O, and their addition salts.

19 Claims, No Drawings

15-DEOXYSPERGUALIN ANALOGS, THEIR METHOD OF PREPARATION AND THEIR USE IN THERAPEUTICS

FIELD OF THE INVENTION

The present invention relates to novel compounds which are structurally related to 15-deoxyspergualin. It further relates to their method of preparation and to their use in therapeutics as immunosuppressants.

PRIOR ART

It is known that 15-deoxyspergualin is a derivative of spergualin, the latter being an antibiotic isolated from a culture of *Bacillus laterosporus*. The first studies of 15-deoxyspergualin revealed an anti-tumoral activity; later, the study of its activity in the field of immunosuppression became predominant.

In this connection, reference may be made especially to the following publications: G. DICKNEITE, "15-Deoxyspergualin: From Cytostasis to Immunosuppression", Behring Inst. Mitt., no. 82, 231–239 (1988); G. DICKNEITE, "The Influence of (±)-15-Deoxyspergualin on Experimental Transplantation and its Immunopharmacological Mode of Action", Behring Inst. Mitt., no 80, 93–102 (1986); and K. NEMOTO, "Deoxyspergualin in lethal murine graft-versus-host disease", Transplantation vol. 51, 712–715, no. 3, Mar. 1991.

Despite its true activity in the field of immunosuppression, 15-deoxyspergualin does not have a satisfactory chemical stability. Attempts have therefore been made to obtain more stable derivatives, in particular by replacing the α-hydroxyglycine residue of deoxyspergualin with various α- or ω-amino acids.

In this connection, reference may be made especially to R. NISHIZAWA, "Synthesis and biological activity of spergualin analogues", J. Antibiotics 1988, 42(11), 1629–1643, and to EP-A-0 105 193.

SUBJECT OF THE INVENTION

Novel 15-deoxyspergualin analogs are now proposed which are structurally different from the products proposed in EP-A-0 105 193, are chemically stable and have a greater activity in the field of immunosuppression than the known products of the prior art.

The notable difference between the products according to the invention and the known products of the prior art, from the point of view of chemical structure, is the inversion of the CO—NH bond linking the guanidinehexyl or guanidineoctyl residue to the central amino acid.

The 15-deoxyspergualin-analogous compounds according to the invention are selected from the group consisting of:
(i) the compounds of the formula

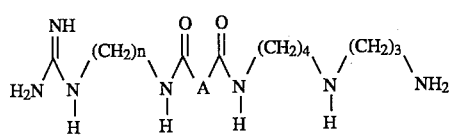

in which:
n is equal to 6 or 8 and

A is a single bond, a group $CH_2$, a group $CH(OH)$, a group $CHF$, a group $CH(OCH_3)$, a group $CH_2NH$ or a group $CH_2O$, and
(ii) their addition salts.

According to the invention, a method of preparing the compounds of formula I and their addition salts is also proposed, said method comprising the deprotection of a compound of the formula

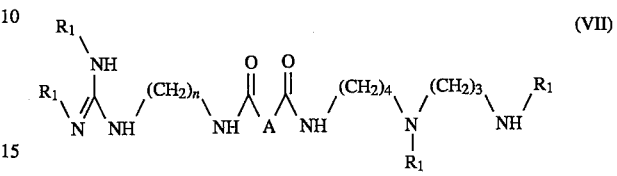

in which n and A are defined as indicated above and $R_1$ is a protecting group for an amine function, especially by means of a strong acid in order to replace $R_1$ with H.

The use of an immunosuppressive substance selected from the group consisting of the compounds of formula I and their non-toxic addition salts is also proposed for the preparation of a drug intended for use in therapeutics to combat immune disorders.

Finally, the use of a substance selected from the group consisting of the compounds of formula I and their non-toxic addition salts is proposed for the preparation of drugs intended for the treatment of malaria.

Of course, in such uses, the active ingredient will be present in a therapeutically effective amount.

DETAILED DESCRIPTION OF THE INVENTION

Addition salts are understood as meaning the acid addition salts obtained by reacting a mineral acid or an organic acid with a compound of formula I. The preferred mineral acids for salification are hydrochloric, hydrobromic, sulfuric and phosphoric acids. The preferred organic acids for salification are fumaric, maleic, methanesulfonic, oxalic, citric and trifluoroacetic acids.

The compounds of formula I can be prepared by methods known per se by applying conventional reaction mechanisms, such as the formation of an amide bond, and especially by applying the known methods of peptide chemistry.

As indicated above, the method of preparation which is proposed according to the invention comprises the deprotection of a compound of formula VII.

In practical terms, each protecting group $R_1$ which is to be replaced with a hydrogen atom will be a group of the oxycarbonyl type known in the field of peptide synthesis for temporarily blocking "amino" functions which are not totally substituted. The radicals given below together with their conventional abbreviations may be mentioned among the protecting groups which are suitable for this purpose:
Adoc=adamantyloxycarbonyl
Aoc=t-amyloxycarbonyl
Boc=t-butoxycarbonyl (alternative nomenclature: (1,1-dimethylethoxy)carbonyl)
Fmoc=9-fluorenylmethoxycarbonyl
Foc=furfuryloxycarbonyl
Iboc=isobornyloxycarbonyl
Z=benzyloxycarbonyl
Z(p-Cl)=p-chlorobenzyloxycarbonyl
Z(p-OMe)=p-methoxybenzyloxycarbonyl Among these groups, which are referred to as "aminoprotecting" groups in the remainder of the text, the preferred group $R_1$ according to the invention is the group Boc.

Again in practical terms, the method of preparing a compound of formula I or one of its addition salts is selected from the group consisting of:

variant A, which comprises steps consisting in:
(i) reacting a compound of the formula

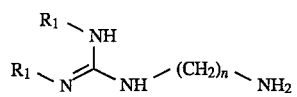

(II)

in which n is equal to 6 or 8 and $R_1$ is an amino-protecting group, especially the (1,1-dimethylethoxy)carbonyl group, with an acid or an acid chloride of the formula

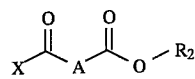

(III)

in which:

X is a chlorine atom or a group OH,

A is a single bond, a group $CH_2$, a group CHF, a group $CH(OCH_2C_6H_5)$ or a group $CH(OCH_3)$ and $R_2$ is a linear or branched $C_1$–$C_3$-alkyl group or a phenylmethyl group, in an organic solvent (especially a chlorinated solvent such as, for example, dichloromethane or chloroform), in the presence of a carboxy group activator (especially a carbodiimide such as, for example, 1,3-dicyclohexylcarbodiimide) and in the presence of a nucleophilic agent (especially 1-hydroxybenzotriazole), at a temperature between 0° C. and about 40° C., at a rate of about 1 mol of II to about 1 mol of III, to give a compound of the formula

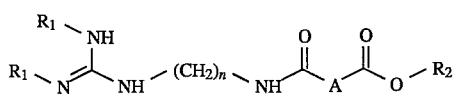

(IV)

in which $R_1$, $R_2$ and n are defined as indicated above and A is a single bond, $CH_2$, CHF, $CH(OCH_2C_6H_5)$ or $CH(OCH_3)$, (ii) saponifying the resulting compound of formula IV in an organic solvent, in the presence of a strong base, to give a compound of the formula

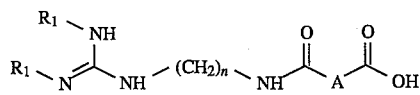

(V)

in which $R_1$ and n are defined as indicated above and A is a single bond, $CH_2$, CHF, $CH(OCH_2C_6H_5)$ or $CH(OCH_3)$, (iii) condensing the resulting compound of formula V with an amine of the formula

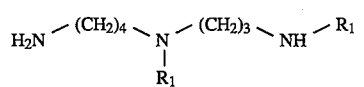

(VI)

in which $R_1$ is defined as indicated above, under conditions identical to those of step (i) above, to give a compound of the formula

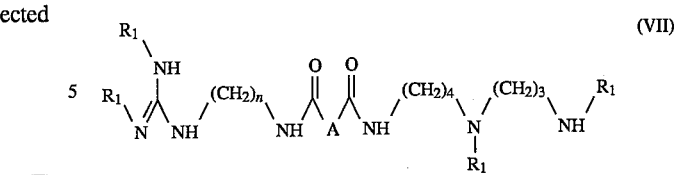

(VII)

in which $R_1$ and n are defined as indicated above and A is a single bond, $CH_2$, CHF, $CH(OCH_2C_6H_5)$ or $CH(OCH_3)$, (iv) if necessary, deprotecting the compound of formula VII in which A is the group $CH(OCH_2C_6H_5)$ by catalytic hydrogenation to give the compound of formula VII in which A is the group CH(OH), (v) deprotecting the compound VII obtained in step (iii) or (iv) where A is a single bond, $CH_2$, CHF, CH(OH) or $CH(OCH_3)$ to remove the protecting group $R_1$, especially by reaction with a strong acid such as, for example, trifluoroacetic acid, thereby giving an addition salt of a compound of formula I where A is a single bond, $CH_2$, CHF, CH(OH) or $CH(OCH_3)$, and (vi) if necessary, obtaining said compound of formula I in the form of the free base by reaction with a strong base, and then obtaining the other addition salts from said free base;

variant B, which comprises steps consisting in:
(i) reacting a compound of the formula

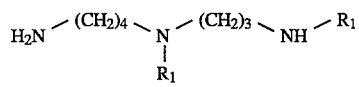

(VI)

in which $R_1$ is a protecting group as indicated above [especially (1,1-dimethylethoxy)carbonyl], with an acid or an acid chloride of the formula

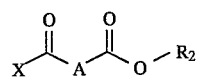

(III)

in which:

X is a chlorine atom or a group OH,

A is a single bond, a group $CH_2$, a group $CH(OCH_2C_6H_5)$, a group $CH(OCH_3)$ or a group CHF and $R_2$ is a linear or branched $C_1$–$C_3$-alkyl group or a phenylmethyl group, in an organic solvent (especially a chlorinated solvent such as, for example, dichloromethane or chloroform), in the presence of a carboxy group activator (especially a carbodiimide such as, for example, 1,3-dicyclohexylcarbodiimide) and in the presence of a nucleophilic agent (especially 1-hydroxybenzotriazole), at a temperature between 0° C. and about 40° C., at a rate of about 1 mol of VI to about 1 mol of III, to give a compound of the formula

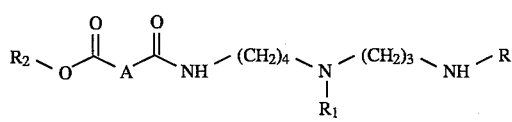

(VIII)

in which $R_1$ and $R_2$ are defined as indicated above and A is a single bond, $CH_2$, a group $CH(OCH_2C_6H_5)$, a group $CH(OCH_3)$ or a group CHF, (ii) saponifying the resulting compound of formula VIII in an organic solvent, in the presence of a strong base, to give a compound of the formula

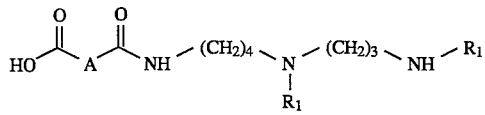                                                                 (IX)

in which $R_1$ is defined as indicated above and A is a single bond, $CH_2$, a group $CH(OCH_2C_6H_5)$, a group $CH(OCH_3)$ or a group CHF, (iii) condensing the resulting compound of formula IX with an amine of the formula

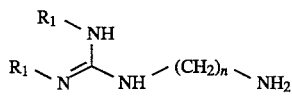                                                                 (II)

in which n is equal to 6 or 8 and $R_1$ is defined as indicated above, under conditions identical to those of step (i) above, to give a compound of the formula

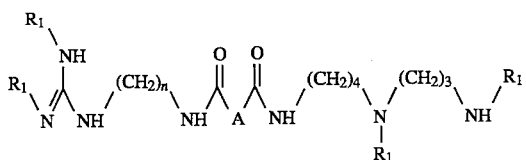                                                                 (VII)

in which $R_1$ and n are defined as indicated above and A is a single bond, $CH_2$, a group $CH(OCH_2C_6H_5)$, a group $CH(OCH_3)$ or a group CHF, (iv) if necessary, deprotecting the compound of formula VII in which A is the group $CH(OCH_2C_6H_5)$ by catalytic hydrogenation to give the compound of formula VII in which A is the group CH(OH), (v) deprotecting the resulting compound VII by reaction with a strong acid (especially trifluoroacetic acid) to give an addition salt of a compound of formula I where A is a single bond, $CH_2$, CH(OH), $CH(OCH_3)$ or a group CHF, and (vi) if necessary, obtaining said compound of formula I in the form of the free base by reaction with a strong base, and then obtaining the other addition salts from said free base;

variant c, which comprises steps consisting in:
(i) acylating the $NH_2$-terminal end of a base of the formula

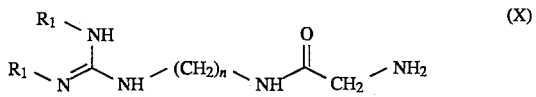                                                                 (X)

in which $R_1$ is a protecting group as indicated above [especially (1,1-dimethylethoxy)carbonyl] and n is equal to 6 or 8, with a chloroformate or a symmetrical carbonate [especially bis(4-nitrophenyl) carbonate], in an inert solvent, at room temperature (15°–25° C.), (ii) aminolyzing the resulting compound with an amine of the formula

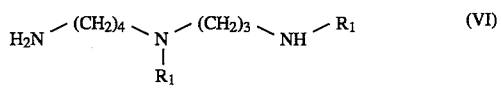                                                                 (VI)

in which $R_1$ is defined as indicated above, to give a compound of the formula

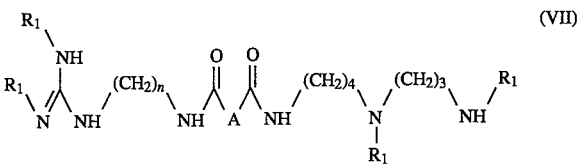                                                                 (VII)

in which $R_1$ and n are defined as indicated above and A is the group $CH_2NH$, (iii) deprotecting the resulting compound VII by reaction with a strong acid (especially trifluoroacetic acid) to give an addition salt of a compound of formula I where A is $CH_2NH$, and (iv) if necessary, obtaining said compound of formula I in the form of the free base by reaction with a strong base, and then obtaining the other addition salts from said free base; and variant D, which comprises steps consisting in:
(i) reacting a compound of the formula

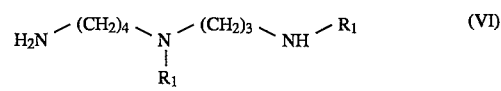                                                                 (VI)

in which $R_1$ is an amino-protecting group as indicated above [especially (1,1-dimethylethoxy)carbonyl], with a carbonate of the formula

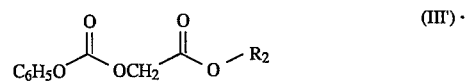                                                                 (III')

in which:
$R_2$ is a linear or branched $C_1$–$C_3$-alkyl group or a phenylmethyl group,
in an inert organic solvent (especially an aromatic solvent such as, for example, toluene), at the reflux temperature of the reaction medium, at a rate of about 1 mol of VI to about 1 mol of III', to give a compound of the formula

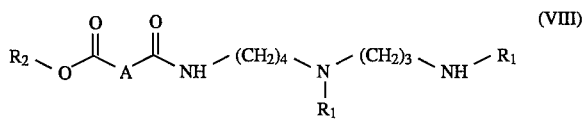                                                                 (VIII)

in which $R_1$ and $R_2$ are defined as indicated above and A is the group $CH_2O$, (ii) saponifying the resulting compound of formula VIII in an organic solvent, in the presence of a strong base, to give a compound of the formula

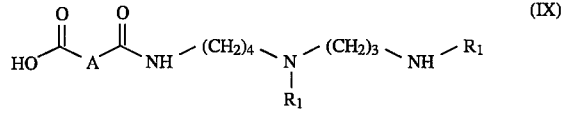                                                                (IX)

in which $R_1$ is defined as indicated above and A is $CH_2O$, (iii) condensing the resulting compound of formula IX with an amine of the formula

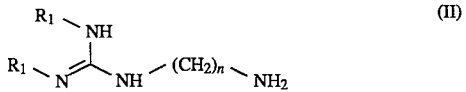                                                                (II)

in which $R_1$ is defined as indicated above and n is equal to 6 or 8, in an organic solvent (especially a chlorinated solvent such as, for example, dichloromethane or chloroform), in the presence of a carboxy group activator (especially a carbodiimide such as, for example, 1,3-dicyclohexylcarbodiimide) and in the presence of a nucleophilic agent (especially 1-hydroxybenzotriazole), at a temperature between 0° C. and about 40° C., at a rate of about 1 mol of IX to about 1 mol of II, to give a compound of the formula

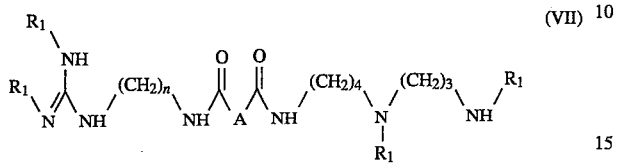 (VII)

in which $R_1$ and n are defined as indicated above and A is $CH_2O$, (iv) deprotecting the resulting compound VII by reaction with a strong acid (especially trifluoroacetic acid) to give an addition salt of a compound of formula I where A is $CH_2O$, and (v) if necessary, obtaining said compound of formula I in the form of the free base by reaction with a strong base, and then obtaining the other addition salts from said free base.

The compound VI where $R_1$ is a (1,1-dimethylethoxy)carbonyl group can be obtained by the method proposed by Raymond J. BERGERON, "Total Synthesis of (±)-15-Deoxyspergualin", J. Org. Chem. 1987, 52, 1700–1703.

It is also possible to obtain the compounds of formula IV by generating and then aminolyzing a mixed anhydride: the acid of formula III is reacted with a chloroformate, especially isobutyl chloroformate, in the presence of one equivalent of a tertiary base, especially N-methylmorpholine, in an unreactive solvent, at a temperature of about −30° C., for about 0.5 hour, and the base II is then added to the reaction medium.

The formation of an amide bond can also be effected by the methods known to those skilled in the art, especially by the acylation of an appropriate amine with an acid chloride in an unreactive solvent, in the presence of a strong organic base.

The intermediates of formula VII in which $R_1$ is an amino-protecting group, especially of the oxycarbonyl type, n is equal to 6 or 8 and A is a single bond, a group $CH_2$, a group $CH(OH)$, a group $CH(OCH_3)$, a group $CH_2NH$, a group $CH_2O$, a group $CH(OCH_2C_6H_5)$ or a group $CHF$ are novel compounds and form a further subject of the invention.

The invention will be understood more clearly from the description of the Examples which follow and the pharmacological results obtained with the compounds according to the invention, compared with the results obtained with the known products of the prior art. The nomenclature used below is that proposed by Chemical Abstracts; according to this nomenclature, a diester of the type t-butyl ethyl alkanedioate is referred to here as "(1,1-dimethylethyl) ethyl alkanedioate".

PREPARATION I

Bis(1,1-dimethylethyl) [[(6-aminohexyl)imino]methylene]biscarbamate 17.23 g (0,148 mol) of hexane-1,6-diamine are added at room temperature, with stirring, to a solution of 43 g (0,148 mol) of N,N'-bis(tert-butoxycarbonyl)-S-methylisothiourea in 300 ml of tetrahydrofuran. The reaction medium is stirred for 16 hours. After evaporation of the solvent, the residue obtained is chromatographed on silica using a $CHCl_3$/ethanol mixture (3/1 v/v) and then an ethyl acetate/methanol/32% aqueous ammonia mixture (6/3/0.1 v/v/v) as the eluent to give 19.7 g (yield: 37%) of a yellow oil.

$^1$H NMR ($CDCl_3$): 1.25–1.60 (m, 28H); 2.7 (t, 2H); 3.5 (q, 2H); 8.3 (t, 1H); 11.5 (s, 1H).

The product below is obtained by following an analogous procedure:

Bis(1,1-dimethylethyl) [[(8-aminooctyl)imino]methylene] biscarbamate $^1$H M ($CDCl_3$): 1.3–1.7 (m, 32H); 2.7 (t, 2H); 3.4 (q, 2H); 8.3 (t, 1H); 11.5 (s, 1H).

PREPARATION II 1-(1,1-Dimethylethyl) 14-ethyl 6-[(1,1-dimethylethoxy)carbonyl]-12-oxo-2,6,11 -triazatetradecanedioate 0.82 g (4×10⁻³ mol) of 1,3-dicyclohexylcarbodiimide is added to a solution, cooled to 0° C., of 0.53 g (4×10⁻³ mol) of ethyl malonate in 20 ml of anhydrous chloroform.

After stirring for 0.5 hour, a solution of 1.04 g (3×10⁻³ mol) of 1,1-dimethylethyl 10-amino-6-[(1,1-dimethylethoxy)carbonyl]-2,6 -diazadecanoate in 5 ml of anhydrous chloroform is added dropwise at 0° C. The mixture is stirred for 5 hours at room temperature and 1.06 g (8×10⁻³ mol) of ethyl malonate and 1.64 g (8×10⁻³ mol) of 1,3-dicyclohexylcarbodiimide are added. The mixture is stirred for 1 hour and the solvent is evaporated off under reduced pressure. The pasty residue obtained is chromatographed on silica using an ethyl acetate/hexane mixture (1/1 v/v) and then ethyl acetate as the eluent to give 0.95 g (yield: 69%) of the expected product in the form of an oil.

$^1$H NMR ($CDCl_3$): 1.25 (t, 3H); 1.40–1.70 (m, 24H); 3.10–3.35 (m, 10H); 4.2 (q, 2H).

PREPARATION III 1-(1,1-Dimethylethyl) 6-[(1,1-dimethylethoxy)carbonyl]-12-oxo-2,6,11-triazatetradecanedioate 0.95 g (2.07×10⁻³ mol) of the product obtained in Preparation II is dissolved in a mixture of 20 ml of N sodium hydroxide and 20 ml of dimethoxyethane (1/1 v/v). The reaction mixture is stirred for 15 minutes at room temperature, reduced by one third of its volume and then acidified to a pH of between 2 and 3 with 1N hydrochloric acid. This is followed by extraction with twice 50 ml of chloroform. After evaporation of the organic phases under reduced pressure, the residue obtained is chromatographed on silica using an ethyl acetate/methanol mixture (3/1 v/v) and then methanol as the eluent to give 0.75 g (yield: 84%) of the expected product in the form of an oil.

$^1$H NMR (dimethyl sulfoxide-$d_6$): 1.40 (s, 18H); 1.55 (m, 6H); 2.90 (m, 4H); 3.15 (m, 6H).

PREPARATION IV

Bis(1,1-dimethylethyl) 3-[[(1,1-dimethylethoxy)carbonyl]amino]-20 -[(1,1-dimethylethoxy) carbonyl]-12,14-dioxo-2,4,11,15,20,24- hexaazapentacos-2-enedioate 0.46 g (2.32×10⁻³ mol) of 1,3-dicyclohexylcarbodiimide and 0.0155 g (0.1×10⁻³ mol) of 1-hydroxybenzotriazole hydrate are added, with stirring, to a solution at 0° C. of 0.5 g (1.16×10⁻³ mol) of the product obtained in Preparation III in 30 ml of anhydrous chloroform. After the reaction medium has been stirred for 0.5 hour, 0.42 g (1.16×10⁻³ mol) of bis(1,1-dimethylethyl) [[(6-aminohexyl)imino]methylene]biscarbamate (obtained by the method of Preparation I above) is added dropwise at 0° C. The reaction medium is stirred again at 0° C. for 1.5 hours, 0.23 g ($1.16 \times 10^{-3}$ mol) of 1,3-dicyclohexylcarbodiimide is then added and stirring is continued for 24 hours at room temperature. The solvent is evaporated off under reduced pressure and the residue obtained is chromatographed on silica using an ethyl acetate/hexane mixture (1/1 v/v), then ethyl acetate and finally an ethyl acetate/methanol mixture (9/1 v/v) as the eluent to give 0.7 g (yield: 73%) of the expected product in the form of an oil.

$^1$H NMR (CDCl$_3$): 1.3–1.7 (m, 50H); 3.1–3.3 (m, 12H); 3.4 (q, 2H); 4.8 and 5.3 (s broad, 1H); 6.8 and 7.15 (s broad, 2H); 8.3 (t, 1H); 11.5 (s, 1H).

EXAMPLE 1

N-[4-[[3-(Amino)propyl]amino]butyl]-N'-[6-[(aminoiminomethyl)amino]hexyl]propanediamide tris(trifluoroacetate)

0.7 g ($0.9 \times 10^{-3}$ mol) of the product obtained in Preparation IV is dissolved in 10 ml of trifluoroacetic acid and 10 ml of anhydrous dichloromethane. The reaction medium is stirred for 24 hours at room temperature and the solvent is then evaporated off under reduced pressure. The residue obtained is taken up in 150 ml of distilled water and then lyophilized. The residue is purified by MPLC (medium pressure liquid chromatography) on a reversed phase (RP18 silica) using a water/acetonitrile/trifluoroacetic acid mixture (7/2/1 v/v/v) as the eluent to give 0.43 g (yield: 66%) of a very hygroscopic solid.

$^1$H NMR (dimethyl sulfoxide-d$_6$): 1.2–1.6 (m, 12H); 1.9 (m, 2H); 2.9–3.1 (m, 14H); 7.2 (s broad, 4H); 7.7 (t, 1H); 8 (m, 5H); 8.7 (s broad, 2H).

$^{13}$C NMR (dimethyl sulfoxide-d$_6$): 22.5; 23.4; 25.4; 25.6; 25.7; 28.0; 28.5; 35.8; 37.6; 38.2; 40.3; 43.0; 43.5; 46.1; 156.6; 166.9 (2C).

PREPARATION V 1-(1,1-Dimethylethyl) 16-ethyl 3-[[(1,1-dimethylethoxy)carbonyl]amino]-14-oxo-2,4,13-triazahexadec-2-enedioate 1.96 g (yield: 75%) of the expected product are obtained in the form of an oil by following a procedure analogous to Preparation IV and starting from 1.32 g ($10 \times 10^{-3}$ mol) of ethyl malonate and 2 g ($5.18 \times 10^{-3}$ mol) of bis(1,1-dimethylethyl) [[(8-aminooctyl)imino]methylene]biscarbamate.

$^1$H NMR (CDCl$_3$): 1.25–1.70 (m, 33H); 3.25 (q, 2H); 3.30 (s, 2H); 3.40 (q, 2H); 4.2 (q, 2H); 7.25 (s, 1H); 8.3 (s, 1H); 11.5 (s, 1H).

PREPARATION VI 1-(1,1-Dimethylethyl) 3-[[(1,1-dimethylethoxy)carbonyl]amino]-14-oxo-2,4,13-triazahexadec-2-enedioate 1.92 g (yield: 100%) of the expected product are obtained in the form of an oil by following a procedure analogous to Preparation III and starting from 1.96 g ($3.92 \times 10^{-3}$ mol) of the product obtained in Preparation V.

$^1$H NMR (CDCl$_3$): 1.25–1.70 (m, 30H); 3.27–3.39 (m, 6H); 7.25 (s, 1H); 8.40 (s, 1H).

PREPARATION VII

Bis(1,1-dimethylethyl) 3-[[(1,1-dimethylethoxy)carbonyl]amino]-22-[(1,1-dimethylethoxy)carbonyl]-14,16-dioxo-2,4,13,17,22,26-hexaazaheptacos-2-enedioate 0.41 g (yield: 13%) of the expected product is obtained in the form of an oil by following a procedure analogous to Preparation IV and starting from 1.85 g ($3.92 \times 10^{-3}$ mol) of the product obtained in Preparation VI and 1.35 g ($3.92 \times 10^{-3}$ mol) of 1,1-dimethylethyl 10-amino-6-[(1,1-dimethylethoxy)carbonyl]-2,6-diazadecanoate.

$^1$H NMR (CDCl$_3$): 1.30–1.70 (m, 54H); 3.1–3.5 (m, 14H); 4.8 and 5.3 (s broad, 1H); 6.7 and 7.1 (s broad, 2H); 8.3 (t, 1H); 11.5 (s, 1H).

EXAMPLE 2

N-[4-[[3-(Amino)propyl]amino]butyl]-N'-[8-[(aminoiminomethyl)amino]octyl]propanediamide tris(trifluoroacetate)

0.24 g (yield: 65%) of the expected product is obtained in the form of an oil by following a procedure analogous to the method of Example 1 and starting from 0.41 g ($0.51 \times 10^{-3}$ mol) of the product obtained in Preparation VII.

$^1$H NMR (dimethyl sulfoxide-d$_6$): 1.2–1.6 (m, 16H); 1.9 (m, 2H); 2.9–3.1 (m, 14H); 7.2 (s broad, 4H); 7.7 (t, 1H); 8 (m, 5H); 8.7 (s broad, 2H).

$^{13}$C NMR (dimethyl sulfoxide-d$_6$): 22.9; 23.7; 26.0; 26.1; 26.3; 28.4; 28.5; 28.6; 28.9; 36.2; 37.9; 38.6; 40.7; 43.3; 43.8; 46.4; 156.8; 166.7; 166.9.

PREPARATION VIII 1-(1,1-Dimethylethyl) 14-methyl 3-[[(1,1-dimethylethoxy)carbonyl]amino]-13-methoxy-12-oxo-2,4,11-triazatetradec-2-enedioate 4.8 g (yield: 87%) of the expected product are obtained in the form of an oil by following a procedure analogous to Preparation IV, starting from 1.8 g ($12 \times 10^{-3}$ mol) of methyl 2-methoxypropanedioate and 4 g ($11 \times 10^{-3}$ mol) of bis(1,1-dimethylethyl) [[(6-aminohexyl)imino]methylene]biscarbamate and replacing the chloroform with dichloromethane.

$^1$H NMR (CDCl$_3$): 1.35–1.65 (m, 26H); 3.2 (m, 2H); 3.35 (q, 2H); 3.45 (s, 3H); 3.8 (s, 3H); 4.3 (s, 1H); 6.7 (t, 1H); 8.3 (t, 1H); 11.5 (s, 1H).

PREPARATION IX 1-(1,1-Dimethylethyl) 3-[[(1,1-dimethylethoxy)carbonyl]amino]-13-methoxy-12-oxo-2,4,11-triazatetradec-2-enedioate 4 g (yield: 89%) of the expected product are obtained in the form of an oil by following a procedure analogous to Preparation III and starting from 4.6 g ($9.4 \times 10^{-3}$ mol) of the product obtained in Preparation VIII.

$^1$H NMR (CDCl$_3$): 1.3–1.65 (m, 26H); 3.1–3.5 (m, 4H); 3.6 (s, 3H); 4.3 (s, 1H); 6.7 (t, 1H); 8.4 (t, 1H); 11.5 (s broad, 1H).

PREPARATION X

Bis(1,1-dimethylethyl) 3-[[(1,1-dimethylethoxy)carbonyl]amino]-20-[(1,1-dimethylethoxy)carbonyl]-13-methoxy-12,14-dioxo-2,4,11,15,20,24-hexaazapentacos-2-enedioate 4 g (yield: 63%) of the expected product are obtained in the form of an oil by following a procedure analogous to Preparation IV, starting from 3.77 g ($8\times10^{-3}$ mol) of the product obtained in Preparation IX and 2.7 g ($8\times10^{-3}$ mol) of 1,1-dimethylethyl 10-amino-6-[(1,1-dimethylethoxy)carbonyl]-2,6-diazadecanoate and replacing the chloroform with dichloromethane.

$^1$H NMR (CDCl$_3$): 1.3–1.8 (m, 50H); 3.0–3.45 (m, 12H); 3.6 (s, 3H); 4.1 (m, 1H); 4.8 and 5.3 (s broad, 1H); 6.9 (s broad, 2H); 8.3 (t, 1H); 11.5 (s, 1H ).

EXAMPLE 3

N-[4-[[3-(Amino)propyl]amino]butyl]-N'-[6-[(aminoiminomethyl)amino]hexyl]-2-methoxypropanediamide tris(trifluoroacetate)

2.86 g (yield: 89%) of the expected product are obtained in the form of an oil by following a procedure analogous to the method of Example 1 and starting from 3.47 g ($4.3\times10^{-3}$ mol) of the product obtained in Preparation X.

$^1$H NMR (dimethyl sulfoxide-d$_6$): 1.25–1.70 (m, 12H); 1.9 (m, 2H); 2.85–3.2 (m, 12H); 3.25 (s, 3H); 4.1 (s, 1H); 6.8–8.7 (m, 12H).

$^{13}$C NMR (CD$_3$OD): 24.2; 25.3; 27.36; 27.37; 29.9; 30.2; 37.9; 39.2; 40.2; 42.5; 45.7; 58.6; 158.7; 169.4; 169.8.

PREPARATION XI

1-(1,1-Dimethylethyl) 14-methyl 6-[(1,1-dimethylethoxy)carbonyl]-13-methoxy-12-oxo-2,6,11-triazatetradecanedioate 1.5 g (yield: 18%) of the expected product are obtained in the form of an oil by following a procedure analogous to Preparation IV and starting from 2.62 g ($17.7\times10^{-3}$ mol) of methyl 2-methoxypropanedioate and 3.45 g ($10\times10^{-3}$ mol) of 1,1-dimethylethyl 10-amino-6-[(1,1-dimethylethoxy)carbonyl]-2,6 -diazadecanoate.

$^1$H NMR (CDCl$_3$): 1.4–1.8 (m, 24H); 3.1–3.4 (m, 8H); 3.5 (s, 3H); 3.8 (s, 3H); 4.3 (s, 1H); 4.8 and 5.3 (s broad, 1H); 6.7 (s, 1H).

PREPARATION XII

1-(1,1-Dimethylethyl) 6-[(1,1-dimethylethoxy)carbonyl]-13 -methoxy-12-oxo-2,6-11-triazatetradecanedioate 1.18 g (yield: 81%) of the expected product are obtained in the form of an oil by following a procedure analogous to Preparation III and starting from 1.5 g ($3.16\times10^{-3}$ mol) of the product obtained in Preparation XI.

$^1$H NMR (CDCl$_3$): 1.4–1.8 (m, 24H); 3.15–3.35 (m, 8H); 3.5 (s, 3H); 4.3 (s, lit); 5.2–5.7 (ds, 1}I); 6.3–6.9 (ds, 1H).

PREPARATION XIII

Bis(1,1-dimethylethyl) 3-[[(1,1-dimethylethoxy)carbonyl]amino]-22-[(1,1-dimethylethoxy)carbonyl]-15-methoxy-14,16-dioxo-2,4,13,17,22,26-hexaazaheptacos-2-enedioate 1.4 g (yield: 65%) of the expected product are obtained in the form of an oil by following a procedure analogous to Preparation IV and starting from 1.18 g ($2.56\times10^{-3}$ mol) of the product obtained in Preparation XII.

$^1$H NMR (CDCl$_3$): 1.3–1.8 (m, 54H); 3.1–3.7 (m, 15H); 4.1 (s, 1H); 4.8 and 5.3 (s broad, 1H); 6.9 (s broad, 2H); 8.3 (t, 1H); 11.5 (s, 1H).

EXAMPLE 4

N-[4-[[3-(Amino)propyl]amino]butyl]-2-methoxy-N'-[8-[(aminoiminomethyl)amino]octyl]propanediamide tris(trifluoroacetate)

0.89 g (yield: 70%) of the expected product is obtained in the form of an oil by following a procedure analogous to the method of Example 1 and starting from 1.37 g ($1.65\times10^{-3}$ mol) of the product obtained in Preparation XIII.

$^1$H NMR (dimethyl sulfoxide-d$_6$): 1.2–1.7 (m, 16H); 1.9 (m, 2H); 2.9–3.10 (m, 12H); 3.3 (s, 3H); 4.1 (s, 1H); 6.8–8.7 (m, 12H).

$^{13}$C NMR (D$_2$O): 23.8; 25.0; 26.5; 27.0; 27.3; 28.5; 29.1 (2C); 37.5; 39.8; 40.2; 42.5; 45.1; 48.2; 58.4; 63.9; 82.5; 157.8; 169.8; 170.2.

PREPARATION XIV

1-(1,1-Dimethylethyl) 15-methyl 6-[(1,1-dimethylethoxy)carbonyl]-13-oxa-12-oxo-2,6,11-triazapentadecanedioate A solution of 7.4 g ($21.4\times10^{-3}$ mol) of 1,1-dimethylethyl 10-amino-6-[(1,1-dimethylethoxy)carbonyl]-2,6-diazadecanoate in 20 ml of toluene is added, with stirring, to a solution of 4.5 g ($21.4\times10^{-3}$ mol) of methyl [(phenoxycarbonyl)oxy]acetate in 100 ml of toluene. The reaction medium is refluxed for 15 hours. The solvent is evaporated off under reduced pressure and the residue obtained is purified by chromatography on silica using a methylcyclohexane/ethyl acetate mixture (7/3 v/v) and then ethyl acetate as the eluent to give 8.4 g (yield: 85%) of the expected product in the form of an oil.

$^1$H NMR (CDCl$_3$): 1.45–1.65 (m, 24H); 3.05–3.25 (m, 8H); 3.8 (s, 3H); 4.7 (s, 2H); 4.9 and 5.3 (s broad, 1H).

PREPARATION XV

1-(1,1-Dimethylethyl) 6-[(1,1-dimethylethoxy)carbonyl]-13-oxa-12-oxo-2,6,11-triazapentadecanedioate 6.7 g (yield: 81%) of the expected product are obtained in the form of an oil by following a procedure analogous to Preparation III and starting from 8.45 g ($18.3\times10^{-3}$ mol) of the product obtained in Preparation XIV.

$^1$H NMR (CDCl$_3$): 1.3–1.8 (m, 24H); 3.10–3.25 (m, 8H); 4.7 (s, 2H); 5.0 (t, 1H); 6.8 (s, 1H).

PREPARATION XVI

Bis(1,1-dimethylethyl)
3-[[(1,1-dimethylethoxy)carbonyl]amino]-21-[(1,1
-dimethylethoxy)carbonyl]-14-oxa-12,15-dioxo-
2,4,11,16,21,25-hexaazahexacos-2-enedioate 3.85 g (yield: 73%) of the expected product are obtained in the form of an oil by following a procedure analogous to Preparation IV and starting from 3 g ($6.7 \times 10^{-3}$ mol) of the product obtained in Preparation XV and 2.4 g ($6.7 \times 10^{-3}$ mol) of bis(1,1-dimethylethyl) [[(6-aminohexyl)imino]methylene]biscarbamate.

$^1$H NMR (CDCl$_3$, D$_2$O): 1.35–1.65 (m, 50H); 3.10–3.30 (m, 12H); 4.55 (s, 2H); 5.2–5.5 (s broad, 1H); 6.4 (s broad, 1H).

PREPARATION XVII

Bis(1,1-dimethylethyl)
3-[[(1,1-dimethylethoxy)carbonyl]amino]-23-[(1,1
-dimethylethoxy)carbonyl]-16-oxa-14,17-dioxo-
2,4,13,18,23,27-hexaazaoctacos-2-enedioate 1.56 g (yield: 57%) of the expected product are obtained in the form of an oil by following a procedure analogous to Preparation IV and starting from 1.5 g ($3.35 \times 10^{-3}$ mol) of the product obtained in Preparation XV and 1.3 g ($3.35 \times 10^{-3}$ mol) of bis(1,1-dimethylethyl) [[(8-aminooctyl)imino]methylene]biscarbamate.

$^1$H NMR (CDCl$_3$): 1.40–1.60 (m, 54H); 3.10–3.40 (m, 12H); 4.5 (s, 2H); 5.1–5.4 (s broad, 1H); 6.3 (s broad, 1H); 8.3 (t, 1H); 11.5 (s broad, 1H).

EXAMPLE 5

2-[[[4-[[3
-(Amino)propyl]amino]butyl]amino]carbonyloxy]
-N-[6-[(aminoiminomethyl) amino]hexyl]acetamide
tris(trifluoroacetate)

2.61 g (yield: 72%) of the expected product are obtained in the form of an oil by following a procedure analogous to the method of Example 1 and starting from 3.85 g ($4.9 \times 10^{-3}$ mol) of the product obtained in Preparation XVI.

$^1$H NMR (dimethyl sulfoxide-d$_6$): 1.25–1.55 (m, 12H); 1.9 (m, 2H); 2.80–3.10 (m, 12H); 4.35 (s, 2H); 5.5–8.6 (m, 12H).

$^{13}$C NMR (D$_2$O): 23.6; 24.5; 26.2; 26.3; 26.7; 28.6; 29.0; 37.3: 39.8; 40.6: 41.9; 45.2; 48.2; 63.7; 157.5; 158.2; 171.4.

EXAMPLE 6

2-[[[4-[[3-
(Amino)propyl]amino]butyl]amino]carbonyloxy]-N-[8
-[(aminoiminomethyl)amino]octyl]acetamide
tris(trifluoroacetate)

0.96 g (yield: 66%) of the expected product is obtained in the form of an oil by following a procedure analogous to the method of Example 1 and starting from 1.56 g ($1.9 \times 10^{-3}$ mol) of the product obtained in Preparation XVII.

$^1$H NMR (dimethyl sulfoxide-d$_6$): 1.2–1.6 (m, 16H); 1.9 (m: 2H); 2.8–3.2 (m, 12H); 4.35 (s, 2H); 6.8–8.6 (m, 12H).

$^{13}$C NMR (D$_2$O): 23.6; 24.5; 26.5; 26.6; 26.7; 28.6; 28.9 (2C); 29.0; 37.9; 40.0; 40.6; 41.9; 45.2; 48.2; 64.7; 158.0; 159.0; 172.1.

PREPARATION XVIII 1-(1,1-Dimethylethyl) 14-ethyl
3-[[(1,1-dimethylethoxy)carbonyl]
amino]-13-phenylmethoxy-12-oxo-2,4,11-
triazatetradec-2-enedioate 1.57 g (yield: 50%) of the expected product are obtained in the form of an oil by following a procedure analogous to Preparation IV and starting from 1.3 g ($5.46 \times 10^{-3}$ mol) of ethyl 2-phenylmethoxypropanedioate and 1.95 g ($5.46 \times 10^{-3}$ mol) of bis(1,1-dimethylethyl) [[(6-aminohexyl)imino]methylene]biscarbamate.

$^1$H NMR (CDCl$_3$): 1.2–1.8 (m, 29H); 3.25 (q, 2H); 3.4 (q, 2H); 4.2 (q, 2H); 4.4 (s, 1H); 4.5–4.8 (dd, 2H); 6.7 (s, 1H); 7.3 (s, 5H); 8.3 (t, 1H); 11.5 (s, 1H).

PREPARATION XIX 1-(1,1-Dimethylethyl)
3-[[(1,1-dimethylethoxy)carbonyl]
amino]-13-phenylmethoxy-12-oxo-2,4,11-
triazatetradec-2-enedioate 1.4 g (yield: 94%) of the expected product are obtained in the form of a yellowish oil by following a procedure analogous to Preparation III and starting from 1.57 g ($2.72 \times 10^{-3}$ mol) of the product obtained in Preparation XVIII.

$^1$H NMR (CDCl$_3$): 1.2–1.8 (m, 26H); 3.2–3.5 (m, 4H); 4.4 (s, 1H); 4.6–5.0 (dd, 2H); 6.8 (s, 1H); 7.3 (s, 5H); 8.3 (t, 1H).

PREPARATION XX

Bis(1,1-dimethylethyl)
3-[[(1,1-dimethylethoxy)carbonyl]amino]-20-[(1,1
-dimethylethoxy)carbonyl]-12,14-dioxo-13-
phenylmethoxy-2,4,11,15,20,24-hexaazapentacos-2-
enedioate 2.1 g (yield: 94%) of the expected product are obtained in the form of an oil by following a procedure analogous to Preparation IV and starting from 1.4 g ($2.54 \times 10^{-3}$ mol) of the product obtained in Preparation XIX and 0.88 g ($2.54 \times 10^{-3}$ mol) of 1,1-dimethylethyl 10-amino-6-[(1,1-dimethylethoxy)carbonyl]-2,6-diazadecanoate.

$^1$H NMR (CDCl$_3$): 1.3–1.8 (m, 50H); 3.1–3.5 (m, 12H); 4.3 (s, 1H); 4.8 (s, 2H); 6.8–7.0 (m, 2H); 7.3 (s, 5H); 8.3 (t, 1H); 11.5 (s, 1H).

PREPARATION XXI

Bis(1,1-dimethylethyl)
3-[[(1,1-dimethylethoxy)carbonyl]amino]-20-[(1,1
-dimethylethoxy)carbonyl]-13-hydroxy-12,14-dioxo-
2,4,11,15,20,24-hexaazapentacos-2-enedioate 0.1 g of 10% palladium-on-charcoal is added to a solution of 1.27 g ($1.45 \times 10^{-3}$ mol) of the product obtained in Preparation XX in 120 ml of ethanol. The mixture is stirred at room temperature and under a hydrogen atmosphere for 2 hours at atmospheric pressure. The catalyst is then filtered off and the organic phase is evaporated to give 1 g (yield: 88%) of an oily residue, which is used without further purification for the preparation of the product of Example 7.

$^1$H NMR (CDCl$_3$): 1.2–1.8 (m, 50H); 3.1–3.6 (m, 12H); 4.3 (s, 1H); 4.6–5.3 (s broad, 3H); 8.3 (s, 1H); 11.5 (s, 1H).

EXAMPLE 7

N-[4-[[3-(Amino)propyl]amino]butyl]-2-hydroxy-N'-[6[(aminoiminomethyl)amino]hexyl]propanediamide tris(trifluoroacetate)

0.6 g (yield: 65%) of the expected product is obtained in the form of an oil by following a procedure analogous to the method of Example 1 and starting from 1 g ($1.27 \times 10^{-3}$ mol) of the product obtained in Preparation XXI.

$^1$H NMR (dimethyl sulfoxide-$d_6$): 1.2–1.6 (m, 12H); 1.85 (m, 2H); 2.7–3.2 (m, 12H); 4.3 (s, 1H); 6.8–8.6 (m, 12H).

$^{13}$C NMR ($D_2O$): 23.5; 24.4; 26.0; 26.1; 26.2; 28.4; 28.8; 37.2; 39.1; 39.9; 41.7; 45.1; 48.0; 73.0; 154.8; 171.1; 171.4.

PREPARATION XXII 1-(1,1-Dimethylethyl) 15-phenylmethyl 3-[[(1,1-dimethylethoxy)carbonyl]amino]-12-oxo-2,4,11,14-tetraazapentadec-2-enedioate A solution of 1.6 g ($14 \times 10^{-3}$ mol) of isobutyl chloroformate in 5 ml of tetrahydrofuran is added dropwise to a solution, cooled to $-30°$ C., of 3 g ($14 \times 10^{-3}$ mol) of carbobenzyloxyglycine and 2.8 g ($28 \times 10^{-3}$ mol) of N-methylmorpholine in 50 ml of tetrahydrofuran. The reaction medium is stirred for 0.5 hour and a solution of 5.4 g ($14 \times 10^{-3}$ mol) of bis(1,1-dimethylethyl) [[(6-aminohexyl)imino]methylene]biscarbamate in 20 ml of tetrahydrofuran is added. Stirring is continued for 2 hours at $-30°$ C. and then for 24 hours at room temperature. After filtration of the reaction medium and evaporation of the filtrate under reduced pressure, the residue obtained is purified by chromatography on silica using an ethyl acetate/methylcyclohexane mixture (1/1 v/v) as the eluent to give 7.16 g (yield: 91%) of the expected product in the form of an oil.

$^1$H NMR ($CDCl_3$): 1.3–1.7 (m, 26H); 3.2 (q, 2H); 3.4 (q, 2H); 3. S (d, 2H); 5.15 (s, 2H); 5.5 (s broad, 1H); 6.0 (s broad, 1H ); 7.3 (s, 5H).

PREPARATION XXIII 1,1-Dimethylethyl 13-amino-3-[[(1,1-dimethylethoxy)carbonyl]amino]-12-oxo-2,4,11-triazatridec-2-enoate 5.3 g (yield: 98%) of the expected product are obtained in the form of an oil by following a procedure analogous to Preparation XXI and starting from 7.1 g ($13 \times 10^{-3}$ mol) of the product obtained in Preparation XXII.

$^1$NMR ($CDCl_3$): 1.3–1.6 (m, 28H); 3.25–3.45 (m, 6H); 7.3 (s, 1H); 8.3 (t, 1H); 11.5 (s, 1H).

PREPARATION XXIV

Bis(1,1-dimethylethyl) 3-[[(1,1-dimethylethoxy)carbonyl]amino]-21-[(1,1-dimethylethoxy)carbonyl]-12,15-dioxo-2,4,11,14,16,21,25-heptaazahexacos-2-enedioate 4.3 g ($13 \times 10^{-3}$ mol) of bis(4-nitrophenyl) carbonate are added in small portions to a solution of 5.3 g ($12 \times 10^{-3}$ mol) of the product obtained in Preparation XXIII in 50 ml of anhydrous tetrahydrofuran. The reaction medium is stirred for 1 hour at room temperature and a solution of 4.5 g ($13 \times 10^{-3}$ mol) of 1,1-dimethylethyl 10-amino-6-[(1,1-dimethylethoxy)carbonyl]-2,6-diazadecanoate in 50 ml of anhydrous tetrahydrofuran is added dropwise. Stirring is continued for 24 hours at room temperature and the solvent is evaporated off under reduced pressure. The residue obtained is purified by chromatography on silica using ethyl acetate as the eluent to give 6.01 g (yield: 64%) of the expected product in the form of an oil.

$^1$H NMR ($CDCl_3$): 1.3–1.7 (m, 50H); 3.1–3.35 (m, 12H); 3.8 (d, 2H); 4.8 and 5.8 (s broad, 3H); 6.9 (t, 1H); 8.3 (t, 1H); 11.5 (s, 1H).

EXAMPLE 8

N-[4-[[3-(Amino)propyl]amino]butyl]-N'-[[[[6-[(aminoiminomethyl)amino] hexyl]amino]carbonyl]methyl]urea tris(trifluoroacetate)

4.75 g (yield: 86%) of the expected product are obtained in the form of an oil by following a procedure analogous to the method of Example 1 and starting from 6 g ($7.6 \times 10^{-3}$ mol) of the product obtained in Preparation XXIV.

$^1$H NMR (dimethyl sulfoxide-$d_6$): 1.2–1.65 (m, 12H); 1.9 (m, 2H); 2.9–3.15 (m, 12H); 3.6 (d, 2H); 6.1 (t, 1H); 6.3 (t, 1H); 6.8–9 (m, 11H).

$^{13}$C NMR (dimethyl sulfoxide-$d_6$): 22.8; 23.7; 25.6; 25.8; 27.0; 28.3; 28.9; 36.1; 38.3; 38.5; 40.5; 42.7; 43.7; 46.5; 156.7; 157.9; 169.6.

PREPARATION XXV 1-(1,1-Dimethylethyl) 17-phenylmethyl 3-[[(1,1-dimethylethoxy)carbonyl] amino]-14-oxo-2,4,13,16-tetraazaheptadec-2-enedioate 2.33 g (yield: 74%) of the expected product are obtained in the form of an oil by following a procedure analogous to Preparation IV and starting from 1.35 g ($6.47 \times 10^{-3}$ mol) of carbobenzyloxyglycine and 2 g ($5.18 \times 10^{-3}$ mol) of bis(1,1-dimethylethyl) [[(8-aminooctyl)imino]methylene]biscarbamate.

$^1$H NMR ($CDCl_3$): 1.25–1.70 (m, 30H); 3.25 (q, 2H); 3.4 (q, 2H); 3.8 (d, 2H); 5.15 (s, 2H); 5.5 (s broad, 1H); 6.0 (s broad, 1H); 7.3 (s, 5H); 8.3 (t, 1H); 11.5 (s, 1H).

PREPARATION XXVI 1,1-Dimethylethyl 15-amino-3-[[(1,1-dimethylethoxy)carbonyl] amino]-14-oxo-2,4,13-triazapentadec-2-enoate 2.16 g (yield: 100%) of the expected product are obtained in the form of an oil by following a procedure analogous to Preparation XXI and starting from 2.33 g ($4.04 \times 10^{-3}$ mol) of the product obtained in Preparation XXV.

$^1$H NMR ($CDCl_3$): 1.3–1.8 (m, 32H); 3.25–3.45 (m, 6H); 7.3 (s, 1H); 8.3 (t, 1H); 11.5 (s, 1H).

PREPARATION XXVII

Bis(1,1-dimethylethyl) 3-[[(1,1-dimethylethoxy)carbonyl]amino]-23-[(1,1-dimethylethoxy)carbonyl]-14,17-dioxo-2,4,13,16,18,23,27-heptaazaoctacos-2-enedioate 1.5 g (yield: 45%) of the expected product are obtained in the form of an oil by following a procedure analogous to Preparation XXIV and starting from 1.79 g ($4.04 \times 10^{-3}$ mol) of the product obtained in Preparation XXVI.

$^1$H NMR (CDCl$_3$): 1.3–1.7 (m, 54H); 3.1–3.4 (m, 12H); 3.8 (d, 2H); 4.8, 5.2 and 5.7 (s broad, 2H); 6.0 and 6.7 (s broad, 1H); 8.3 (t, 1H); 11.5 (s, 1H).

EXAMPLE 9

N-[4-[[3-(Amino)propyl]amino]butyl]-N'-[[[[8-[(aminoiminomethyl)amino]octyl]amino]carbonyl]methyl]urea tris(trifluoroacetate)

1.14 g (yield: 82%) of the expected product are obtained in the form of an oil by following a procedure analogous to the method of Example 1 and starting from 1.5 g (1.84×10$^{-3}$ mol) of the product obtained in Preparation XXVII.

$^1$H NMR (dimethyl sulfoxide-d$_6$): 1.25–1.55 (m, 16H); 1.9 (m, 2H); 2.9–3.10 (m, 12H); 3.6 (s, 2H); 6.0–6.3 (s broad, 2H); 6.8–8.6 (m, 11H).

$^{13}$C NMR (dimethyl sulfoxide-d$_6$): 22.9; 23.8; 26.0; 26.3; 27.1; 28.4; 28.5; 28.6; 29.1; 36.2; 38.4; 38.7; 40.7; 42.7; 43.8; 46.6; 156.7; 158.0; 169.6.

PREPARATION XXVIII 1-(1,1-Dimethylethyl) 3-[[(1,1-dimethylethoxy)carbonyl]amino]-12-oxo-2,4,11-triazatridec-2-enedioate A solution of 0.67 g (5×10$^{-3}$ mol) of the acid chloride of ethyl oxalate in 5 ml of dichloromethane is added dropwise to a solution of 1.6 g (4.5×10$^{-3}$ mol) of bis(1,1-dimethylethyl) [[(6-aminohexyl)imino]methylene]biscarbamate and 0.6 g (6×10$^{-3}$ mol) of triethylamine in 10 ml of anhydrous dichloromethane. The mixture is stirred for 1 hour at room temperature, the solvent is then evaporated off under reduced pressure and the residue obtained is chromatographed on silica using a hexane/ethyl acetate mixture (2/1 v/v) as the eluent to give 1.68 g (yield: 82%) of the expected product in the form of an oil.

$^1$H NMR (CDCl$_3$): 1.3–1.7 (m, 29H); 3.3–3.4 (m, 4H); 4.4 (q, 2H); 7.1 (t, 1H); 8.3 (t, 1H); 11.5 (s, 1H).

PREPARATION XXIX 1-(1,1-Dimethylethyl) 3-[[(1,1-dimethylethoxy)carbonyl]amino]-12-oxo-2,4,11-triazatridec-2-enedioate 1.2 g (yield: 75%) of the expected product are obtained in the form of an oil by following a procedure analogous to Preparation III and starting from 1.67 g (3.7×10$^{-3}$ mol) of the product obtained in Preparation XXVIII.

$^1$H NMR (CDCl$_3$): 1.25–1.7 (m, 26H); 3.3–3.5 (m, 4H); 7.4 (t, 1H); 8.5 (t, 1H); 11.5 (s broad, 1H).

PREPARATION XXX

Bis(1,1-dimethylethyl) 3-[[(1,1-dimethylethoxy)carbonyl]amino]-19-[(1,1-dimethylethoxy)carbonyl]-12,13-dioxo-2,4,11,14,19,23-hexaazatetracos-2-enedioate 1.2 g (yield: 53%) of the expected product are obtained in the form of an oil by following a procedure analogous to Preparation XXII and starting from 1.4 g (3.5×10$^{-3}$ mol) of the product obtained in Preparation XXIX and 1.05 g (3×10$^{-3}$ mol) of 1,1-dimethylethyl 10-amino-6-[(1,1-dimethylethoxy/carbonyl]-2,6-diazadecanoate.

$^1$H NMR (CDCl$_3$): 1.3–1.7 (m, 50H); 3.1–3.4 (m, 12H); 4.8 and 5.3 (s broad, 1H); 7.5 (m, 2H); 8.3 (t, 1H); 11.5 (s, 1H).

EXAMPLE 10

N-[4-[[3-(Amino)propyl]amino]butyl]-N'-[6-[(aminoiminomethyl)amino]hexyl]ethanediamide tris(trifluoroacetate)

1.05 g (yield: 95%) of the expected product are obtained in the form of an oil by following a procedure analogous to the method of Example 1 and starting from 1.2 g (1.6×10$^{-3}$ mol) of the product obtained in Preparation XXX.

$^1$H NMR (dimethyl sulfoxide-d$_6$): 1.3–1.65 (m, 12H); 1.9 (m, 2H); 2.8–3.3 (m, 12H); 6.8–9.9 (m, 12H).

$^{13}$C NMR (dimethyl sulfoxide-d$_6$, D$_2$O): 23.9; 24.7; 26.3; 26.4; 26.5; 28.7; 29.0; 37.5; 39.7; 40.4; 42.0; 45.4; 48.1; 157.7; 161.8; 162.1.

PREPARATION XXXI 1-(1,1-Dimethylethyl) 13-ethyl 6-[(1,1-dimethylethoxy)carbonyl]-12-oxo-2,6,11-triazatridecanedioate 2.31 g (yield: 89%) of the expected product are obtained in the form of an oil by following a procedure analogous to Preparation XXVIII and starting from 2 g (5.8×10$^{-3}$ mol) of 1,1-dimethylethyl 10-amino-6-[(1,1-dimethylethoxy)carbonyl]-2,6-diazadecanoate and 1.03 g (7.54×10$^{-3}$ mol) of the acid chloride of ethyl oxalate.

$^1$H NMR (CDCl$_3$): 1.25–1.65 (m, 27H); 3.1–3.35 (m, 8H); 4.35 (q, 2H); 4.75 and 5.25 (s broad, 1H); 7.2 (s, 1H).

PREPARATION XXXII 1-(1,1-Dimethylethyl) 6-[(1,1-dimethylethoxy)carbonyl]-12-oxo-2,6,11-triazatridecanedioate 2.16 g (yield: 100%) of the expected product are obtained in the form of an oil by following a procedure analogous to Preparation III and starting from 2.31 g (5.19×10$^{-3}$ mol) of the product obtained in Preparation XXXI.

$^1$H NMR (CDCl$_3$): 1.25–1.70 (m, 24H); 3.1–3.4 (m, 8H); 4.8–5.25 (ds, 1H); 7.5 (s broad, 1H).

PREPARATION XXXIII

Bis(1,1-dimethylethyl) 3-[[(1,1-dimethylethoxy)carbonyl]amino]-21-[(1,1-dimethylethoxy)carbonyl]-14,15-dioxo-2,4,13,16,21,25-hexaazahexacos-2-enedioate 0.9 g (yield: 48%) of the expected product is obtained in the form of an oil by following a procedure analogous to Preparation IV and starting from 1 g (2.4×10$^{-3}$ mol) of the product obtained in Preparation XXXII and 0.92 g (2.4×10$^{-3}$ mol) of bis(1,1-dimethylethyl) [[(8-aminooctyl)imino]methylene]biscarbamate.

$^1$H NMR (CDCl$_3$): 1.3 (t, 3H); 1.4–1.7 (m, 24H); 3.0–3.4 (m, 8H); 4.25 (q, 2H); 4.4 (s, 1H); 4.5–4.7 (2d, 2H); 5.0 (s, 1H); 6.7 (s, 1H); 7.3 (m, 5H).

EXAMPLE 11

N-[4-[[3-(Amino)propyl]amino]butyl]-N'-[8-[(aminoiminomethyl)amino]octyl]ethanediamide tris(trifluoroacetate)

0.15 g (yield: 18%) of the expected product is obtained in the form of an oil by following a procedure analogous to the method of Example 1 and starting from 0.9 g ($1.15 \times 10^{-3}$ mol) of the product obtained in Preparation XXXIII.

$^1$H NMR (dimethyl sulfoxide-$d_6$): 1.25–1.50 (m, 16H); 1.9 (m, 2H); 2.9–3.15 (m, 12H); 6.9–8.8 (m, 12H).

$^{13}$C NMR ($D_2O$): 23.8; 24.5; 26.1; 26.5; 26.7; 28.6; 28.92; 28.95; 29.0; 37.3; 39.5; 40.4; 42.0; 45.2; 48.1.

PREPARATION XXXIV

1-(1,1-Dimethylethyl) 14-ethyl 6-[(1,1-dimethylethoxy)carbonyl] -12-oxo-13-phenylmethoxy-2,6,11-triazatetradecanedioate The expected product is obtained with a yield of 35%, after purification by chromatography on silica (eluent: methylcyclohexane 8/ethyl acetate 2), by following a procedure analogous to Preparation IV and starting from 3 g ($12.6 \times 10^{-3}$ mol) of ethyl 2-(phenylmethoxy)propanedioate and 4.4 g ($12.6 \times 10^{-3}$ mol) of 1,1-dimethylethyl 10-amino-6-[(1,1-dimethylethoxy)carbonyl]-2,6-diazadecanoate.

$^1$H NMR ($CDCl_3$): 1.3 (t, 3H); 1.4–1.7 (m, 24H); 3.0–3.4 (m, 8H); 4.25 (q, 2H); 4.4 (s, 1H); 4.5–4.7 (2d, 2H); 5.0 (s, 1H); 6.7 (s, 1H); 7.3 (m, 5H).

PREPARATION XXXV

1-(1,1-Dimethylethyl) 6-[(1,1-dimethylethoxy)carbonyl]-12-oxo-13-phenylmethoxy-2,6,11-triazatetradecanedioate 2.46 g ($4.3 \times 10^{-3}$ mol) of the product obtained in Preparation XXXIV are dissolved in an ethanol/water mixture (1/1 by volume) and 258 mg of sodium hydroxide are added. The reaction medium is stirred at room temperature for 24 hours, 10 ml of water and 20 ml of chloroform are then added and the mixture is acidified to pH 2 with N hydrochloric acid. It is extracted with chloroform and, after drying over magnesium sulfate, the organic phase is concentrated under reduced pressure to give the expected product with a yield of 76%.

$^1$H NMR ($CDCl_3$): 1.4–1.7 (m, 24H); 3.0–3.3 (m, 8H); 4.4–4.5 (m, 1H); 4.7–5.1 (2d, 2H); 5.0 (s, 1H); 6.65 (s, 1H); 7.4 (m, 5H).

PREPARATION XXXVI

Bis(1,1-dimethylethyl) 3-[[(1,1-dimethylethoxy)carbonyl]amino]-22-[(1,1-dimethylethoxy)carbonyl]-14,16-dioxo-15-phenylmethoxy-2,4,13,17,22,26-hexaazaheptacos-2-enedioate The expected product is obtained in the form of an oil with a yield of 59%, after purification by chromatography on silica (eluent: methylcyclohexane 7/ethyl acetate 3), by following a procedure analogous to Preparation IV and starting from 1.67 g ($3.11 \times 10^{-3}$ mol) of the product of Preparation XXXV and 1.20 g ($3.11 \cdot 10^{-3}$ mol) of bis(1,1-dimethylethyl) [[(8-aminooctyl)imino]methylene]biscarbamate.

$^1$H NMR ($CDCl_3$): 1.2–1.8 (m, 54H); 3.0–3.5 (m, 12H); 4.3 (s, 1H); 4.8 (m, 2H); 5.1 (s, 1H); 6.9–7.1 (m, 2H); 7.4 (m, 5H); 8.3 (t, 1H); 11.5 (s, 1H).

PREPARATION XXXVII

Bis(1,1-dimethylethyl) 3-[[(1,1-dimethylethoxy)carbonyl]amino]-22-[(1,1-dimethylethoxy)carbonyl]-14,16-dioxo-15-hydroxy-2,4,13,17,22,26-hexaazaheptacos-2-enedioate The expected product is obtained with a yield of 55% by following a procedure analogous to Preparation XXI and starting from 1.64 g of the product obtained in Preparation XXXVI.

$^1$H NMR ($CDCl_3$): 1.3–1.7 (m, 54H); 3.0–3.4 (m, 8H); 4.4 (s, 1H); 5.0 (s, 1H); 7.2 (s, 1H); 7.35 (s, 1H); 8.3 (t, 1H); 11.5 (s, 1H).

EXAMPLE 12

N-[4-[[3-(Amino)propyl]amino]butyl]-2-hydroxy-N'-[8-[(aminoiminomethyl)amino]octyl]propanediamide tris(trifluoroacetate).

The expected product is obtained in the form of an oil with a yield of 67%, after purification by MPLC on RP18 grafted silica (eluent: water 7.5/acetonitrile 1.5/trifluoroacetic acid 1), by following a procedure analogous to the method of Example 1 and starting from 0.81 g of the product obtained in Preparation XXXVII.

$^1$H NMR (DMSO-$d_6$): 1.1–1.7 (m, 16H); 1.9 (m, 2H); 2.8–3.2 (m, 12H); 4.3 (s, 1H); 6.9–8.7 (m, 12H).

$^{13}$C NMR (DMSO-$d_6$): 14.8; 20.9; 22.2; 23.1; 25.3; 25.9; 28.5; 28.7; 28.9; 36.8; 38.1; 43.8; 46.2; 60.1; 71.8; 157.3; 166.2; 166.5.

PREPARATION XXXVIII

1-(1,1-Dimethylethyl) 14-ethyl 6-[(1,1-dimethylethoxy)carbonyl]-13-fluoro-12-oxo-2,6,11-triazatetradecanedioate A solution of 1.7 g ($11 \times 10^{-3}$ mol) of ethyl 2-fluoropropanedioate and 2.22 g ($22 \times 10^{-3}$ mol) of N-methylmorpholine is prepared in 50 ml of anhydrous tetrahydrofuran (THF) and 5 ml of anhydrous dimethylformamide. The mixture is subsequently cooled to −20° C. and a solution of 1.6 ml ($12 \times 10^{-3}$ mol) of isobutyl chloroformate in 5 ml of THF is then added. The resulting mixture is stirred for 30 min at −20° C. and a solution of 3.9 g ($11 \times 10^{-3}$ mol) of 1,1-dimethylethyl 10-amino-6-[(1,1-dimethylethoxy)carbonyl]-2,6-diazadecanoate in 30 ml of THF is then added. Stirring is continued for 2 hours at −20° C. and then for 12 hours at room temperature. The reaction medium is filtered and the filtrate is concentrated under reduced pressure. The residue obtained is purified by chromatography on silica (eluent: methylcyclohexane 7/ethyl acetate 3) to give the expected product in the form of an oil with a yield of 34%.

$^1$H NMR ($CDCl_3$): 1.34 (t, 3H); 1.4–1.7 (m, 24H); 3.0–3.4 (m, 8H); 4.3 (m, 2H); 5.0 (s, 1H); 5.25 (d, 1H); 6.55 (s, 1H).

PREPARATION XXXIX 1-(1,1-Dimethylethyl)
6-[(1,1-dimethylethoxy)carbonyl]-13-fluoro-12
-oxo-2,6,11-triazatetradecanedioate A solution of 1.8 g ($3.8\times10^{-3}$ mol) of the product obtained in Preparation XXXVIII is prepared in 6 ml of N aqueous sodium hydroxide and 20 ml of dimethoxyethane. After stirring for one hour at room temperature, 10 ml of water and 20 ml of dichloromethane are added and the mixture is acidified to pH 2 with N hydrochloric acid. It is extracted with twice 20 ml of dichloromethane and the organic phase is dried over magnesium sulfate and concentrated under reduced pressure to give 1.55 g of the expected product in the form of an oil (yield: 91%).

$^1$H NMR (CDCl$_3$): 1.4–1.7 (m, 24H); 3.0–3.35 (m, 8H); 5.0 (s, 1H); 5.3 (d, 1H); 6.5 (s, 1H).

PREPARATION XL

Bis(1,1-dimethylethyl)
3-[[(1,1-dimethylethoxy)carbonyl]amino]-20-[(1,1
-dimethylethoxy)carbonyl]-12,14-dioxo-13-fluoro-
2,4,11,15,20,24-hexaazapentacos-2-enedioate A solution of 0.29 ml ($2.2\times10^{-3}$ mol) of isobutyl chloroformate in 5 ml of THF is added dropwise to a solution, cooled to −20° C., of 1 g ($2.2\times10^{-3}$ mol) of the product obtained according to Preparation XXXIX and 4.5 g ($4.4\times10^{-3}$ mol) of N-methylmorpholine in 30 ml of anhydrous THF. The mixture is stirred for 30 min at −20° C. and a solution of 0.876 g ($2.2\times10^{-3}$ mol) of bis(1,1-dimethylethyl) [[(6-aminohexyl)imino]methylene]biscarbamate and 0.34 ml ($2.2\times10^{-3}$ mol) of triethylamine in 5 ml of THF is then added. The temperature is maintained at −20° C. for two hours, the mixture is then brought to room temperature and stirring is continued for 12 hours. The reaction medium is filtered and then concentrated under reduced pressure. The residue is then purified by chromatography on silica (eluent: ethyl acetate 7/cyclohexane 3) to give 1.43 g of the expected product in the form of an oil (yield: 81%).

$^1$H NMR (CDCl$_3$): 1.3–1.7 (m, 50H); 3.0–3.45 (m, 12H); 5.0 (s, 1H); 5.2 (d, 1H); 6.8–7.1 (m, 2H); 8.3 (t, 1H); 11.5 (s, 1H).

EXAMPLE 13

N-[4-[[3-(Amino)propyl]amino]butyl]-N'-[6-
[(aminoiminomethyl)amino]hexyl]
-2-fluoropropanediamide tris(trifluoroacetate)

263 mg of the expected product are obtained in the form of an oil (yield: 71%), after purification by MPLC on RP18 grafted silica (eluent: water 7.5/acetonitrile 2/trifluoroacetic acid 0.5), by following a procedure analogous to the method of Example 1 and starting from 0.4 g ($0.5\times10^{-3}$ mol) of the product obtained in Preparation XL.

$^1$H NMR (DMSO-d$_6$): 1.25–1.55 (m, 12H); 1.9 (m, 2H); 2.7–3.15 (m, 12H); 5.2 (d, 1H); 6.9–8.7 (m, 12H).

$^{13}$C NMR (D$_2$O/dioxane-d$_8$): 23.65; 24.53; 26.17; 26.25; 28.55; 28.79; 37.34; 39.32; 40.08; 41.86; 45.22; 48.09; 87.00; 89.66; 157.0; 166.2; 166.7.

PREPARATION XLI

Bis(1,1-dimethylethyl)
3-[[(1,1-dimethylethoxy)carbonyl]amino]-22-[(1,1
-dimethylethoxy)carbonyl]-15-fluoro-14,16-dioxo-
2,4,13,17,22,26-hexaazaheptacos-2-enedioate 0.513 g of the expected product is obtained in the form of an oil (yield: 61%), after purification by chromatography on silica (eluent: ethyl acetate 6/cyclohexane 4), by following a procedure analogous to Preparation XXII and starting from 0.460 g ($1.02\times10^{-3}$ mol) of the product obtained according to Preparation XXXIX and 0.395 g ($1.02\times10^{-3}$ mol) of bis(1,1-dimethylethyl) [[(8-aminooctyl)imino]methylene] biscarbamate.

$^1$H NMR (CDCl$_3$): 1.2–1.7 (m, 54H); 3.0–3.4 (m, 12H); 5.0 (s, 1Hi; 5.2 (d, 1H); 6.8–7.1 (m, 2H); 8.3 (t, 1H); 11.5 (s, 1H).

EXAMPLE 14

N-[4-[[3-(Amino)propyl]amino]butyl]-2-fluoro-N'-
[8[(aminoiminomethyl)amino]octyl]
propanediamide tris(trifluoroacetate)

The expected product is obtained in the form of an oil, after purification by MPLC on RP18 grafted silica, by following a procedure analogous to Preparation XXII and starting from 0.460 g ($1.02\times10^{-3}$ mol) of the product obtained according to Preparation XLI.

$^1$H NMR (DMSO-d$_6$): 1.25–1.50 (m, 1H); 1.84 (m, 2H); 2.7–3.15 (m, 12H); 5.20 (d, 1H); 6.9–8.7 (m, 12H).

$^{13}$C NMR (D$_2$O/dioxane-d$_8$): 23.66; 24.55; 26.18; 26.28; 26.57; 27.48; 28.86; 37.35; 39.31; 40.21; 40.33; 45.23; 48.10; 87.26–89.86; 157.0; 166.2; 166.7.

EXAMPLE 15

N-[4-[[3-(Amino)propyl]amino]butyl]-N'-[6-
[(aminoiminomethyl)amino]hexyl]propanediamide
tris(hydrochloride)

Method A:

1 g ($1.4\times10^{-3}$ mol) of the product obtained in Example 1 is dissolved in a mixture of 7 ml of 10M hydrochloric acid and 50 ml of distilled water and the solution obtained is then lyophilized. This operation is repeated twice. The lyophilization residue is taken up in a mixture of 9 ml of ethanol and 1 ml of methanol. The crystals obtained after 24 hours at room temperature are filtered off, rinsed with isopropyl ether and dried under vacuum to give the expected product in the form of white crystals with a yield of 68%.

M.p.=130° C.

Method B:

2.5 g ($3.28\times10^{-3}$ mol) of the product obtained according to Preparation IV are dissolved in 25 ml of methanol saturated with hydrogen chloride. After stirring overnight at room temperature, the solution is concentrated under reduced pressure and the residue is redissolved in 10 ml of water and then lyophilized. The resulting compound is recrystallized from an ethanol/methanol mixture (9/1) to give the crystalline product with a yield of 52%.

EXAMPLE 16

2-[[4-[[3-(Amino)propyl]amino]butyl]amino]carbonyloxy]-N-[6-[(aminoiminomethyl)amino]hexyl]acetamide tris(hydrochloride)

The expected product is obtained in the form of crystals with a yield of 58% by following a procedure analogous to the method of Example 15 (method B) and starting from the product obtained according to Preparation XVI.

M.p.=148° C.

The immunosuppressive activity of the products according to the invention was demonstrated with the aid of a test for graft-versus-host reaction. B6D2F1 male mice (C57B1/6×DBA/2 first generation hybrids) are immunosuppressed by means of an intraperitoneal (i.p.) injection of cyclophosphamide. After three days (day 0 of the experiment: D0), they receive $4\times10^7$ C57B1/6 mouse splenocytes by intravenous administration. The animals are then divided into groups of at least 8 and receive a daily treatment from D1 to D5 and from D7 to D10 by i.p. administration. The control group receives the vehicle only. The mortality is followed up to D60. The results, expressed as the mean value of the survival in days at the indicated dose, are collated in Table I, in which the values given are significant according to the Logrank test (probability less than or equal to 5%). For purposes of comparison, Table I also indicates the values obtained with the known products of the prior art: 15-deoxyspergualin (DSG), cyclosporin A, which is currently the reference immunosuppressant used in therapeutics, and the product of Example 1 described in EP-A-0 105 193. This comparison shows that the products according to the invention are up to 250 times more active than the known products of the prior art. In particular, the product of Example 1 according to the invention has a significant activity as from 0.1 mg/kg, whereas the comparative product of Example 1 of EP-A-0 105 193 only has a significant activity from 1 mg/kg, 15-deoxyspergualin from 0.3 mg/kg and cyclosporin A from 25 mg/kg.

Furthermore, the solution stability of the compounds according to the invention is markedly greater than that of the known products of the prior art, especially 15-deoxyspergualin.

The products according to the invention are useful in therapeutics as curative or preventive immunosuppressants, especially in preventing the rejection of vascularized or non-vascularized allogenic or xenogenic organs or the graft-versus-host reaction following a vascularized or non-vascularized graft, in treating genetically defined or acquired autoimmune diseases or chronic inflammatory diseases, as well as in any pathological condition where an immune disorder appears to be the cause or factor responsible for maintaining a degraded clinical state.

The products according to the invention can also be administered in combination with cytotoxic anticancer drugs in order to limit their side-effects, and in combination with the administration of products of biotechnological origin, especially recombinant cytokinins or monoclonal and polyclonal antibodies, in order to reduce the appearance of the protective antibodies produced by the patient.

The products according to the invention can be used as a curative treatment for parasitosis, in particular in the case of malaria.

The products according to the invention can be administered orally, by injection, especially intramuscular or intravenous injection, topically, especially in the form of a cream for local application or eye drops, transdermally, by suppository or by inhalation.

TABLE I

| Example* | n | A | Dose (mg/kg) | Survival (days) |
|---|---|---|---|---|
| 1 | 6 | $CH_2$ | 0.1 | 27.6 |
|  |  |  | 0.3 | 48.5 |
| 2 | 8 | $CH_2$ | 3 | 47.0 |
| 3 | 6 | $CH(OCH_3)$ | 3 | 55.3 |
| 4 | 8 | $CH(OCH_3)$ | 3 | 27.6 |
| 5 | 6 | $CH_2O$ | 3 | 57.9 |
| 7 | 6 | CH(OH) | 3 | 53.0 |
| 8 | 6 | $CH_2NH$ | 0.3 | 39.8 |
| 10 | 6 | single bond | 1 | 52.9 |
| 11 | 8 | single bond | 3 | 59.4 |
| 12 | 8 | CH(OH) | 1 | 55.6 |
| 13 | 6 | CHF | 3 | 60.0 |
| 15-deoxyspergualin |  |  | 1 | 43.1 |
|  |  |  | 0.3 | 32.1 |
| CYCLOSPORIN A |  |  | 25 | 36.0 |
| Ex. 1 of EP-A-0 105 193 |  |  | 1 | 32.0 |

*in the form of the tris(trifluoroacetate) for the products according to the invention

What is claimed is:

1. A compound belonging to the family of 15-deoxyspergualin analogs, which is selected from the group consisting of:

(i) the compounds of the formula

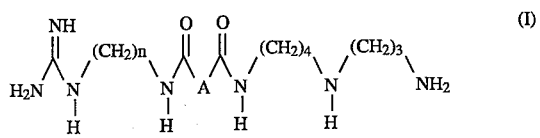

in which:

n is equal to 6 or 8 and

A is a bond, a group $CH_2$, a group CH(OH), a group CHF, a group $CH(OCH_3)$, a group $CH_2NH$ or a group $CH_2O$, and (ii) their nontoxic addition salts.

2. A compound according to claim 1 wherein n is equal to 6 in formula I.

3. A compound according to claim 1 wherein n is equal to 8 in formula I.

4. A compound according to claim 1 wherein A is the group $CH_2O$ in formula I.

5. A compound according to claim 1 wherein A is the group $CH_2$ in formula I.

6. 2-[[[4-[[3-(Amino)propyl]amino]butyl]amino]carbonyloxy]-N-[6-[(aminoiminomethyl)amino]hexyl]acetamide or its addition salt with a mineral or organic acid.

7. N-[4-[[3-(Amino)propyl]amino]butyl]-N'-[6-[(aminoiminomethyl)amino]hexyl]propanediamide or its addition salt with a mineral or organic acid.

8. A composition which contains, in association with a physiologically acceptable excipient, at least one compound according to claim 1.

9. A composition which contains, in association with a physiologically acceptable excipient, at least one compound according to claim 2.

10. A composition which contains, in association with a physiologically acceptable excipient, at least one compound according to claim 3.

11. A composition which contains, in association with a physiologically acceptable excipient, at least one compound according to claim 4.

12. A composition which contains, in association with a physiologically acceptable excipient, at least one compound according to claim 5.

13. A composition which contains, in association with a physiologically acceptable excipient, at least one compound according to claim 6.

14. A composition which contains, in association with a physiologically acceptable excipient, at least one compound according to claim 7.

15. A composition according to claim 14 in which the said compound is present in an immunosuppressant effective amount.

16. A composition according to claim 6 in which the said compound is present in an immunosuppressant effective amount.

17. A composition according to claim 3 in which the said compound is present in an immunosuppressant effective amount.

18. A composition according to claim 2 in which the said compound is present in an immunosuppressant effective amount.

19. A composition according to claim 2 in which the said compound is present in an immunosuppressant effective amount.

* * * * *